United States Patent
Trumbore et al.

(10) Patent No.: US 8,592,380 B2
(45) Date of Patent: Nov. 26, 2013

(54) AEROSOL FOAMS COMPRISING CLINDAMYCIN PHOSPHATE

(75) Inventors: Mark W. Trumbore, Westford, MA (US); Wendy Schilling, Warwick, RI (US); Ravi K. Varanasi, Cumberland, RI (US)

(73) Assignee: Precision Dermatology, Inc., Cumberland, RI (US)

( * ) Notice: Subject to any disclaimer, the term of this patent is extended or adjusted under 35 U.S.C. 154(b) by 260 days.

(21) Appl. No.: 13/053,524

(22) Filed: Mar. 22, 2011

(65) Prior Publication Data

US 2011/0236321 A1    Sep. 29, 2011

Related U.S. Application Data

(60) Provisional application No. 61/318,035, filed on Mar. 26, 2010.

(51) Int. Cl.
*A61K 31/70*    (2006.01)
*A61K 31/7056*  (2006.01)
*A61K 31/40*    (2006.01)

(52) U.S. Cl.
USPC .............................. 514/24; 514/408; 514/859

(58) Field of Classification Search
USPC .......................................... 514/24, 408, 859
See application file for complete search history.

(56) References Cited

U.S. PATENT DOCUMENTS

| | | | |
|---|---|---|---|
| 7,141,237 B2 * | 11/2006 | Abram et al. | 424/45 |
| 2005/0042182 A1 * | 2/2005 | Arkin et al. | 424/47 |
| 2007/0154402 A1 | 7/2007 | Trumbore et al. | |
| 2007/0237724 A1 | 10/2007 | Abram et al. | |
| 2008/0206161 A1 * | 8/2008 | Tamarkin et al. | 424/45 |
| 2008/0253973 A1 | 10/2008 | Tamarkin et al. | |
| 2009/0041686 A1 | 2/2009 | Osborne et al. | |
| 2009/0257957 A1 * | 10/2009 | Burnier et al. | 424/45 |
| 2010/0202978 A1 | 8/2010 | Gurge et al. | |
| 2011/0052506 A1 | 3/2011 | Abel et al. | |

FOREIGN PATENT DOCUMENTS

WO    WO-2008/002646 A2    1/2008

OTHER PUBLICATIONS

Morozowich et al. "Case Study: Clindamycin 2-Phosphate, a prodrug of Clindamycin," In Biotechnology:Pharmaceutical Aspects, Prodrugs: Challenges and Rewards, Part 1, 2007, vol. V, pp. 1207-1219.*
International Search Report and Written Opinion of the International Searching Authority from corresponding PCT application PCT/US2011/029390 filed Mar. 22, 2011.

* cited by examiner

*Primary Examiner* — James H. Alstrum-Acevedo
(74) *Attorney, Agent, or Firm* — Foley Hoag LLP

(57) ABSTRACT

Described herein are emulsions and compositions for the treatment of acne vulgaris. The emulsions may be formulated as aerosol compositions. The aerosol propellant may be a hydrofluoroalkane propellant. The emulsions or compositions may comprise clindamycin phosphate and a buffer salt, and may exhibit decreased rates of clindamycin phosphate hydrolysis. Also described are methods of treating acne vulgaris, comprising the step of applying to an affected area of a subject in need thereof a therapeutically-effective amount of an inventive emulsion or aerosol composition.

11 Claims, 3 Drawing Sheets

Figure 1

| Component (%) | NB120-42 | NB120-43 | NB120-44 | NB120-45 | NB120-49 | NB120-100 | NB216-1 | NB216-2 | NB216-3 | NB216-91 | NB325-27 | NB376-40 | NB367-39 | NB325-25 |
|---|---|---|---|---|---|---|---|---|---|---|---|---|---|---|
| Clindamycin Phosphate | 1.00 | 1.00 | 1.00 | 1.00 | 1.21 | 1.25 | 1.25 | 1.25 | 1.25 | 1.25 | 1.25 | 1.25 | 1.25 | 1.25 |
| Disodium EDTA | 0.10 | 0.10 | 0.10 | 0.10 | 0.10 | 0.10 | 0.10 | 0.10 | 0.10 | 0.10 | 0.10 | 0.10 | 0.10 | 0.10 |
| Glycerin | 12.50 | 10.00 | 10.00 | 10.00 | 12.50 | 12.50 | 12.50 | 12.50 | 5.00 | 20.00 | 12.50 | 12.50 | 12.50 | 12.50 |
| Methylparaben | 0.30 | 0.30 | 0.30 | 0.30 | 0.30 | 0.30 | 0.30 | 0.30 | 0.30 | 0.30 | 0.30 | 0.30 | 0.30 | 0.30 |
| Propylene Glycol | | | | | | | | | 5.00 | | | | | |
| Propylparaben | 0.10 | 0.10 | 0.10 | 0.10 | 0.10 | 0.10 | 0.10 | 0.10 | 0.10 | 0.10 | 0.10 | 0.10 | 0.10 | 0.10 |
| Purified Water | 80.25 | 78.75 | 83.65 | 82.5 | 79.73 | 79.69 | 79.48 | 78.97 | 83.44 | 71.47 | 78.96 | 78.96 | 78.96 | 78.96 |
| Sodium Hydroxide | | | | | 0.01 | 0.01 | 0.02 | 0.03 | 0.01 | 0.03 | 0.03 | 0.03 | 0.03 | 0.03 |
| Sodium Phosphate Monobasic | | | | | 0.30 | 0.30 | 0.50 | 1.00 | 0.30 | 1.00 | 1.00 | 1.00 | 1.00 | 1.00 |
| Cetearyl Alcohol | 2.00 | 2.00 | 2.00 | 2.50 | 2.00 | 2.00 | 2.00 | 2.00 | 1.00 | 2.00 | 0.50 | 0.50 | 0.50 | 4.00 |
| Cyclomethicone | | 5.00 | | | | | | | | | | | | |
| Dimethicone | 1.00 | | | | 1.00 | 1.00 | 1.00 | 1.00 | | 1.00 | 2.00 | 1.00 | | 0.50 |
| Emulsifying Wax | 2.00 | 2.00 | 2.00 | 2.00 | 2.00 | 2.00 | 2.00 | 2.00 | 2.50 | 2.00 | 2.38 | 4.00 | 3.75 | 0.50 |
| Steareth-10 | 0.75 | 0.75 | 0.75 | 0.50 | 0.75 | 0.75 | 0.75 | 0.75 | 1.00 | 0.75 | 0.88 | 0.25 | 1.50 | 0.75 |
| Tocopheryl Acetate | | | 0.10 | | | | | | | | | | | |
| White Petrolatum | | | | 1.00 | | | | | | | | | | |

Figure 2

| Hydrolysis Rate of Clindamycin Phosphate at 20 °C (% / month) | |
|---|---|
| Clindamycin Phosphate in Purified Water | 22.03 |
| Clindamycin Phosphate in Glycerin | 0.18 |
| Clindamycin Phosphate in Phosphate buffer at pH 4.5 | 0.35 |
| Clindamycin Phosphate in Phosphate buffer at pH 5.5 | 0.62 |

Figure 3

| Clindamycin Phosphate Hydrolysis as a Function of Incubation Time (%) | | | | | | | | |
|---|---|---|---|---|---|---|---|---|
| | At 25 °C | | | | At 40 °C | | | |
| | Without Buffer | | With Buffer | | Without Buffer | | With Buffer | |
| Month | NB120-42 | NB120-45 | NB120-100 | NB216-2 | NB120-42 | NB120-45 | NB120-100 | NB216-2 |
| 0 | 0.531 | 0.512 | 0.39 | 0.44 | 0.531 | 0.512 | 0.39 | 0.44 |
| 1 | 1.09 | 1.04 | 0.57 | 0.58 | 3.534 | | 2.86 | 2.9 |
| 2 | 1.56 | 1.53 | 0.68 | 0.77 | 8.23 | 8.06 | 5.39 | 5.6 |
| 3 | | | 1.04 | 1.03 | 10.73 | 10.65 | 8.39 | 8.43 |
| 4 | | | 1.26 | 1.25 | 21.27 | 21.3 | 11.39 | 11.47 |
| 5 | 2.03 | 2.05 | 1.56 | 1.57 | | | 14.36 | 14.45 |
| 6 | | | | | | | | |

| | | Hydrolysis Rate of Clindamycin Phosphate (% / month) | |
|---|---|---|---|
| | | At 25 °C | At 40 °C |
| Without Buffer | NB120-42 | 0.27 | 3.47 |
| | NB120-45 | 0.27 | 3.47 |
| With Buffer | NB120-100 | 0.22 | 2.73 |
| | NB216-2 | 0.21 | 2.74 |

Figure 4

AEROSOL FOAMS COMPRISING CLINDAMYCIN PHOSPHATE

RELATED APPLICATIONS

This application claims the benefit of priority to U.S. Provisional Patent Application Ser. No. 61/318,035, filed Mar. 26, 2010.

BACKGROUND OF THE INVENTION

Acne vulgaris is a pleomorphic skin disease characterized by blackheads, whiteheads, papules, pustules, and cysts. The lesions are often contaminated with bacteria, which can lead to secondary infections. The appearance of acne ranges from slight skin irritation to pitting. In extreme cases, acne leads to the development of disfiguring scars.

Acne vulgaris presents in differing forms which correlate with disease severity. The three common forms of acne vulgaris are Comedonal, Papulo-pustular and Nodular (Nodulocystic). Comedonal acne is characterized by the presence of open and closed comedoes (noninflammatory lesions). Papulo-pustular acne is characterized by inflammatory lesions 5 mm in diameter or less. Nodular acne consists of inflammatory lesions greater than 5 mm in diameter.

Acne severity is classified as "mild" to "severe," depending on the types and numbers of lesions present. Mild acne presents as no more than 19 non-inflammatory lesions, no more than 14 inflammatory lesions, or no more than 29 total lesions. Moderate acne presents as 20-100 non-inflammatory lesions with or without 15-50 inflammatory lesions, for a total of between 30 and 125 lesions. Severe acne presents as greater than 100 non-inflammatory lesions, greater than 50 inflammatory lesions, greater than 125 total lesions, or greater than 5 nodules.

Therapeutic approaches to treating acne include prevention of obstruction of the follicular duct, reopening a blocked duct, combating any infecting bacteria, or reducing the thickened sebum, and combinations of these approaches. The horny outer layer of the skin (stratum corneum) is formed of dead cells, composed largely of keratin. Therapeutic agents which act to prevent the obstruction of the follicular duct by the removal of excess keratin are known as keratolytic agents. Salicylic acid, sulfur, and resorcinol have been employed as keratolytic agents in the management of acne for at least 100 years.

The type of therapy administered for the treatment of acne vulgaris varies with the clinical presentation. Topical treatments are standard for comedones and mild- to moderate-papules and pustules. Oral therapies are generally prescribed for moderate- to severe-papules and pustules and nodular acne. Certain oral contraceptives have proven to be safe and effective for the treatment of acne in women, and may be prescribed for women with acne who also desire birth control.

Prescription topical products indicated for the treatment of acne vulgaris include clindamycin phosphate, erythromycin, sodium sulfacetamide, azaleic acid, benzoyl peroxide, trentinoin, adapalene, tazarotene, clindamycin phosphate-benzoyl peroxide, erythromycin-benzoyl peroxide, and clindamycin phosphate-trentinoin.

Clindamycin is a semi-synthetic antibiotic produced by a 7-(S)-chloro-substitution of the 7-(R)-hydroxyl group of the parent compound lincomycin. Clindamycin phosphate is the water-soluble ester of clindamycin and phosphoric acid, which has little or no antibacterial effect in vitro. The compound is rapidly hydrolyzed both in vitro and in vivo to the active compound, clindamycin, and exerts a potent bacteriostatic effect against streptococci, staphylococci, and anaerobic organisms including *Bacterioides fragilis* and *Propionibacterium acnes*. Its activity against the anaerobe *Propionibacterium acnes* may account for its effectiveness in the treatment of acne vulgaris.

At least one clindamycin phosphate (1%) foam for the treatment of acne vulgaris is currently available, but this product has a number of undesirable properties. The foam is fast-breaking, hydroalcoholic, and thermolabile. As a result of the hydroalcoholic vehicle, the formulation can be drying to the skin and messy to apply, as the foam quickly melts at body temperature. It does not contain any pH-stabilizing buffer salts; indeed U.S. Pat. No. 7,141,237 teaches that the incorporation of buffer salts into clindamycin phosphate foam formulations leads to a dramatic and undesirable increase in the hydrolysis rate of clindamycin phosphate.

Consequently, there exists a need for a clindamycin phosphate foam that is non-drying and not messy, has a suitable melting point, and may be easily applied to the skin.

SUMMARY OF THE INVENTION

In certain embodiments, the invention relates to an emulsion, comprising: an oil phase, wherein the oil phase comprises an emulsifier or surfactant, and a first moisturizer or first emollient; and an aqueous phase, wherein the aqueous phase comprises a vehicle, an antibiotic, a second moisturizer or second emollient, an antioxidant or preservative, a pH adjuster, and a buffer salt.

In certain embodiments, the invention relates to a composition, comprising: an emulsion, wherein the emulsion comprises an oil phase and an aqueous phase; wherein the oil phase comprises an emulsifier or surfactant, and a first moisturizer or first emollient; and the aqueous phase comprises a vehicle, an antibiotic, a second moisturizer or second emollient, an antioxidant or preservative, a pH adjuster, and a buffer salt; a propellant; and a purge gas.

In certain embodiments, the invention relates to a method of treating acne vulgaris, comprising the step of applying to an affected area of a subject in need thereof a therapeutically-effective amount of any one of the aforementioned emulsions or compositions. In certain embodiments, the invention relates to any one of the aforementioned methods, wherein the acne vulgaris is comedonal or papulo-pustular.

BRIEF DESCRIPTION OF THE FIGURES

FIG. 1 tabulates the constituents (and their relative quantities) of various embodiments of the compositions of the invention.

FIG. 2 depicts the hydrolysis rate of clindamycin phosphate in various vehicles.

FIG. 3 depicts the amount of clindamycin phosphate hydrolysis in various compositions of the invention under various experimental conditions.

FIG. 4 depicts the hydrolysis rate of clindamycin phosphate in various compositions of the invention under various experimental conditions.

DETAILED DESCRIPTION OF THE INVENTION

Overview

In certain embodiments, the invention relates to oil-in-water emulsions. In certain embodiments, the compositions do not contain volatile lower alcohols (e.g., ethanol). In certain embodiments, the compositions comprise an aerosol propellant. In certain embodiments, the aerosol propellant is a hydrofluoroalkane (HFA) propellant. In certain embodiments, the compositions comprise a buffer salt. In certain embodiments, the buffer salt helps maintain the composition at a pH compatible with that of normal skin. In certain embodiments, the compositions comprise clindamycin phosphate. In certain embodiments, the addition of a buffer salt to a composition comprising clindamycin phosphate decreases the hydrolysis rate of clindamycin phosphate.

In certain embodiments, the compositions produce a foam upon actuation of an aerosol container charged with the composition. In certain embodiments, the compositions immediately produce a foam upon actuation of an aerosol container charged with the composition. In certain embodiments, the foams are stable against collapse. In certain embodiments, the foams are both time- and temperature-stable. In certain embodiments, the foam is moisturizing. In certain embodiments, the foam is non-irritating. In certain embodiments, the dispensed foam is suitable for the treatment of acne vulgaris. In certain embodiments, the dispensed foam has a density between about 0.05 and about 0.5 g/cm$^3$. In certain embodiments, the foams rub-in quickly without a greasy residue. In certain embodiments, the dispensed foam is easily spread over large body surface areas. In certain embodiments, the foam rapidly collapses when subjected to shear forces, allowing for quick and efficient application to large body surface areas. In certain embodiments, skin moisture levels continue to be improved after application of a composition to the skin, thus reducing the dryness and irritation commonly associated with topical acne medications.

DEFINITIONS

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, a "cream" is an opaque, viscous, non-greasy to mildly-greasy emulsion or suspension semisolid intended for external application to the skin that tends to mostly evaporate or be absorbed when rubbed into the skin. The material contains <50% of hydrocarbons or polyethylene glycols as the vehicle and/or >20% volatiles (as measured by loss on drying to a constant weight at about 105° C.).

As used herein, a "lotion" is an opaque, thin, non-greasy emulsion-based liquid intended for external application to the skin that tends to evaporate rapidly with a cooling sensation when rubbed into the skin. The material generally contains a water based composition with >50% volatiles (as measured by loss on drying to a constant weight at about 105° C.).

Exemplary Constituents of Emulsions and Compositions of the Invention

Exemplary identities of various constituents of the compositions of the present invention are described below.

1. Propellants

There are several possible choices of propellants for an aerosol foam, including, but not limited to, CFCs, hydrocarbons, compressed gases, and HFAs. The Montreal Protocol has banned the use of CFCs (chlorofluorocarbons) due to their ability to deplete the ozone layer. Montreal Protocol on Substances that Deplete the Ozone Layer, United Nations Environmental Programme, 1987. In contrast, hydrocarbon propellants demonstrate very low reactivity and good resistance to free-radical attack. However, hydrocarbon propellants are highly flammable. Moreover, compressed inert gases, such as nitrogen and carbon dioxide, can be used as an aerosol propellant. While offering good chemical stability due to their inertness, they are unable to provide consistent product delivery throughout the life of an aerosol can due to their high vapor pressures. Fortunately, HFAs (hydrofluoroalkanes, also known as hydrofluorocarbons, or HFCs) are pharmaceutically acceptable, generally non-reactive, and ozone-friendly.

In one embodiment, the propellant is a HFA or a mixture of one or more hydrofluoroalkanes. Suitable hydrofluoroalkanes include 1,1,1,2-tetrafluoroethane (HFA 134a); 1,1,1,2,3,3,3-heptafluoropropane (HFA 227); and mixtures and admixtures of these and other HFAs that are currently approved or may become approved for medical use are suitable. Hydrocarbon as well as chlorofluorocarbon (CFC) propellants can also be used in the present invention.

2. Vehicles

Suitable topical vehicles and vehicle components for use with the formulations of the invention are well known in the cosmetic and pharmaceutical arts, and include such vehicles (or vehicle components) as water; organic solvents such as alcohols (particularly lower alcohols readily capable of evaporating from the skin such as ethanol), glycols (such as propylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, dimethiconol and dimethicone copolyol; hydrocarbon-based materials such as petrolatum and squalane; and other vehicles and vehicle components that are suitable for administration to the skin, as well as mixtures of topical vehicle components as identified above or otherwise known to the art.

In one embodiment, the compositions of the present invention are oil-in-water emulsions. Liquids suitable for use in formulating compositions of the present invention include water, and water-miscible solvents such as glycols (e.g., ethylene glycol, butylene glycol, isoprene glycol, propylene glycol), glycerol, liquid polyols, dimethyl sulfoxide, and isopropyl alcohol. One or more aqueous vehicles may be present.

In one embodiment, formulations without methanol, ethanol, propanols, or butanols are desirable.

3. Surfactants and Emulsifiers

Many topical formulations contain chemical emulsions which use surface active ingredients (emulsifiers) to disperse dissimilar chemicals in a particular solvent system. For example, most lipid-like (oily or fatty) or lipophilic ingredients do not uniformly disperse in aqueous solvents unless they are first combined with emulsifiers, which form microscopic aqueous soluble structures (droplets) that contain a lipophilic interior and a hydrophilic exterior, resulting in an oil-in-water emulsion. In order to be soluble in aqueous media, a molecule must be polar or charged so as to favorably interact with water molecules, which are also polar. Similarly, to dissolve an aqueous-soluble polar or charged ingredient in a largely lipid or oil-based solvent, an emulsifier is typically used which forms stable structures that contain the hydrophilic components in the interior of the structure while the exterior is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion droplet. Emulsion destabilization results in the aqueous and lipophilic ingredients separating into two layers, potentially destroying the commercial value of a topical product.

Surfactants suitable for use in the present invention may be ionic or non-ionic. These include, but are not limited to: polysorbates (Polysorbate 20, Polysorbate 40, Polysorbate 60, Polysorbate 80), steareth-10 (Brij 76), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate (dihexadecyl phosphate), ceteareth-10 phosphate, and methylbenzethonium chloride. Appropriate combinations or mixtures of such surfactants may also be used according to the present invention.

Many of these surfactants may also serve as emulsifiers in formulations of the present invention.

Other suitable emulsifiers for use in the formulations of the present invention include, but are not limited to, behentrimonium methosulfate-cetearyl alcohol, non-ionic emulsifiers like emulsifying wax, polyoxyethylene oleyl ether, PEG-40 stearate, cetostearyl alcohol (cetearyl alcohol), ceteareth-12, ceteareth-20, ceteareth-30, ceteareth alcohol, glyceryl stearate, PEG-100 stearate, glyceryl stearate and PEG-100 stearate, steareth-2 and steareth-20, or combinations/mixtures thereof, as well as cationic emulsifiers like stearamidopropyl dimethylamine and behentrimonium methosulfate, or combinations/mixtures thereof.

4. Moisturizers, Emollients, and Humectants

One of the most important aspects of topical products in general, and cosmetic products in particular, is the consumer's perception of the aesthetic qualities of a product. For example, white petrolatum is an excellent moisturizer and skin product, it is rarely used alone, especially on the face, because it is greasy, sticky, does not rub easily into the skin and may soil clothing. Consumers highly value products which are aesthetically elegant and have an acceptable tactile feel and performance on their skin.

Suitable moisturizers for use in the formulations of the present invention include, but are not limited to, lactic acid and other hydroxy acids and their salts, glycerol, propylene glycol, butylene glycol, sodium PCA, sodium hyaluronate, CARBOWAX® 200 polyethylene glycols, CARBOWAX® 400 polyethylene glycols, and CARBOWAX® 800 polyethylene glycols.

Suitable emollients or humectants for use in the formulations of the present invention include, but are not limited to, cetyl palmitate, glycerol (glycerin), PPG-15 stearyl ether, lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, propylene glycol, *Theobroma grandiflorum* seed butter, ceramides (e.g., ceramide 2 or ceramide 3), hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, and dicaprylate/dicaprate.

In addition, appropriate combinations and mixtures of any of these moisturizing agents and emollients may be used in accordance with the present invention.

5. Preservatives and Antioxidants

The composition may further include components adapted to improve the stability or effectiveness of the applied formulation.

Suitable preservatives for use in the present invention include, but are not limited to: ureas, such as imidazolidinyl urea and diazolidinyl urea; phenoxyethanol; sodium methyl paraben, methylparaben, ethylparaben, and propylparaben; potassium sorbate; sodium benzoate; sorbic acid; benzoic acid; formaldehyde; citric acid; sodium citrate; chlorine dioxide; quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; piroctone olamine; *Vitis vinifera* seed oil; and alcoholic agents, for example, chlorobutanol, dichlorobenzyl alcohol, phenylethyl alcohol, and benzyl alcohol.

Suitable antioxidants include, but are not limited to, ascorbic acid and its esters, sodium bisulfite, butylated hydroxytoluene, butylated hydroxyanisole, tocopherols (such as α-tocopherol), tocopheryl acetate, sodium ascorbate/ascorbic acid, ascorbyl palmitate, propyl gallate, and chelating agents like EDTA (e.g., disodium EDTA), citric acid, and sodium citrate.

In certain embodiments, antioxidants or preservatives of the present invention may also function as a moisturizer or emollient, for example.

In addition, combinations or mixtures of these preservatives or anti-oxidants may also be used in the formulations of the present invention.

6. Active Agents

The active agent may be any material that has a desired effect when applied topically to a mammal, particularly a human. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones. Mixtures of any of these active agents may also be employed. Additionally, dermatologically-acceptable salts and esters of any of these agents may be employed.

6.1 Antibiotics

Representative antibiotics include, without limitation, benzoyl peroxide, octopirox, erythromycin, zinc, tetracyclin, triclosan, azelaic acid and its derivatives, phenoxy ethanol and phenoxy propanol, ethyl acetate, clindamycin (e.g., clindamycin phosphate) and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin. Mixtures of these antibiotic agents may also be employed. Additionally, dermatologically-acceptable salts and esters of any of these agents may be employed.

6.2 Non-Steroidal Anti-Inflammatory Agents

Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac, fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamiate, a flufenamic acid derivative, is particularly useful for topical application.

6.3 Steroidal Anti-Inflammatory Agents

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

6.4 Anesthetics

Suitable anesthetics include the aminoacylanilide compounds such as lidocaine, prilocaine, bupivacaine, levo-bupivacaine, ropivacaine, mepivacaine and related local anesthetic compounds having various substituents on the ring system or amine nitrogen; the aminoalkyl benzoate compounds, such as procaine, chloroprocaine, propoxycaine, hexylcaine, tetracaine, cyclomethycaine, benoxinate, butacaine, proparacaine, butamben, and related local anesthetic compounds; cocaine and related local anesthetic compounds; amino carbonate compounds such as diperodon and related local anesthetic compounds; N-phenylamidine compounds such as phenacaine and related anesthetic compounds; N-aminoalkyl amide compounds such as dibucaine and related local anesthetic compounds; aminoketone compounds, such as falicaine, dyclonine and related local anesthetic compounds; and amino ether compounds such as pramoxine, dimethisoquien, and related local anesthetic compounds; and para-amino benzoic acid esters such as benzocaine. Other suitable local anesthetics include ketocaine, dibucaine, amethocaine, propanacaine, and propipocaine.

6.5 Antimicrobial Agents

Suitable antimicrobial agents include, but are not limited to, antibacterial, antifungal, antiprotozoal and antiviral agents, such as beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin (e.g., clindamycin phosphate), ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, famesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

6.6 Keratolytic Agents

Suitable keratolytic agents include, but are not limited to, urea, salicylic acid, papain, sulfur, glycolic acid, pyruvic acid, resorcinol, N-acetylcysteine, retinoids such as retinoic acid and its derivatives (e.g., cis and trans, esters), alpha hydroxy acids, beta hydroxy acids, coal tar, and combinations thereof.

7. Purging Gases

In one embodiment, the air in the container charged with the composition is replaced by an inert gas. In certain embodiments, the inert gas is selected from the group consisting of argon, nitrogen, and mixtures thereof.

8. Buffer Salts

Suitable buffer salts are well-known in the art. Examples of suitable buffer salts include, but are not limited to sodium phosphate monobasic, sodium phosphate dibasic, sodium phosphate tribasic, potassium phosphate monobasic, potassium phosphate dibasic, and potassium phosphate tribasic.

9. Viscosity Modifiers

Suitable viscosity adjusting agents (i.e., thickening and thinning agents) for use in the formulations of the present invention include, but are not limited to, protective colloids or non-ionic gums such as hydroxyethylcellulose, xanthan gum, and sclerotium gum, as well as magnesium aluminum silicate, silica, microcrystalline wax, beeswax, paraffin, and cetyl palmitate. In addition, appropriate combinations or mixtures of these viscosity adjusters may be utilized according to the present invention.

10. Additional Constituents

Additional constituents suitable for incorporation into the emulsions of the present invention include, but are not limited to: skin protectants, adsorbents, demulcents, emollients, moisturizers, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents (e.g., witch hazel, alcohol, and herbal extracts such as chamomile extract), binders/excipients, buffering agents, chelating agents, film forming agents, conditioning agents, opacifying agents, lipids, and pH adjusters (e.g., citric acid, sodium hydroxide, and sodium phosphate).

For example, lipids normally found in healthy skin (or their functional equivalents) may be incorporated into the emulsions of the present invention. In certain embodiments, the lipid is selected from the group consisting of ceramides, cholesterol, and free fatty acids. Examples of lipids include, but are not limited to, ceramide 1, ceramide 2, ceramide 3, ceramide 4, ceramide 5, ceramide 6, hydroxypropyl bispalmitamide MEA, and hydroxypropyl bislauramide MEA, and combinations thereof.

Examples of skin soothing agents include, but are not limited to, allantoin, aloe, avocado oil, green tea extract, hops extract, chamomile extract, colloidal oatmeal, calamine, cucumber extract, and combinations thereof.

Examples of vitamins include, but are not limited to, vitamins A, D, E, K, and combinations thereof.

Examples of sunscreens include, but are not limited to, p-aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide, 4-methylbenzylidene camphor, methylene bis-benzotriazolyl tetramethylbutylphenol, bis-ethylhexyloxyphenol methoxyphenyl triazine, terephthalylidene dicamphor sulfonic acid, drometrizole trisiloxane, disodium phenyl dibenzimidazole tetrasulfonate, diethylamino hydroxybenzoyl hexyl benzoate, octyl triazone, diethylhexyl butamido triazone, polysilicone-15, and combinations thereof.

Suitable fragrances and colors may be used in the formulations of the present invention. Examples of fragrances and colors suitable for use in topical products are known in the art.

Often, one constituent of a composition may accomplish several functions. In one embodiment, the present invention relates to constituents that may act as a lubricant, an emollient, or a skin-penetrating agent. In one embodiment, the multi-functional constituent is socetyl stearate, isopropyl isostearate, isopropyl palmitate, or isopropyl myristate.

Exemplary Emulsions of the Invention

In certain embodiments, the invention relates to an emulsion, comprising:

an oil phase, wherein the oil phase comprises an emulsifier or surfactant, and a first moisturizer or first emollient; and an aqueous phase, wherein the aqueous phase comprises water, an antibiotic, a second moisturizer or second emollient, an antioxidant or preservative, a pH adjuster, and a buffer salt.

In certain embodiments, the invention relates to an emulsion, consisting essentially of:

an oil phase, wherein the oil phase comprises an emulsifier or surfactant, and a first moisturizer or first emollient; and an aqueous phase, wherein the aqueous phase comprises water, an antibiotic, a second moisturizer or second emollient, an antioxidant or preservative, a pH adjuster, and a buffer salt.

In certain embodiments, the invention relates to an emulsion, consisting of:

an oil phase, wherein the oil phase comprises an emulsifier or surfactant, and a first moisturizer or first emollient; and an aqueous phase, wherein the aqueous phase comprises water, an antibiotic, a second moisturizer or second emollient, an antioxidant or preservative, a pH adjuster, and a buffer salt.

In certain embodiments, the invention relates to an emulsion, comprising:
cetearyl alcohol, from about 1% to about 3% by weight of the emulsion;
emulsifying wax, from about 1% to about 3% by weight of the emulsion;
steareth-10, from about 0.3% to about 1.1% by weight of the emulsion;
dimethicone, from about 0.5% to about 1.5% by weight of the emulsion;
water, from about 65% to about 90% by weight of the emulsion;
clindamycin phosphate, from about 0.5% to about 1.8% by weight of the emulsion;
glycerol, from about 6% to about 18% by weight of the emulsion;
disodium EDTA, from about 0.05% to about 0.2% by weight of the emulsion;
methylparaben, from about 0.1% to about 0.5% by weight of the emulsion;
propylparaben, from about 0.05% to about 0.2% by weight of the emulsion;
sodium hydroxide, from about 0.005% to about 0.05% by weight of the emulsion; and
sodium phosphate monobasic, from about 0.1% to about 1.5% by weight of the emulsion.

In certain embodiments, the invention relates to an emulsion, consisting essentially of:
cetearyl alcohol, from about 1% to about 3% by weight of the emulsion;
emulsifying wax, from about 1% to about 3% by weight of the emulsion;
steareth-10, from about 0.3% to about 1.1% by weight of the emulsion;
dimethicone, from about 0.5% to about 1.5% by weight of the emulsion;
water, from about 65% to about 90% by weight of the emulsion;
clindamycin phosphate, from about 0.5% to about 1.8% by weight of the emulsion;
glycerol, from about 6% to about 18% by weight of the emulsion;
disodium EDTA, from about 0.05% to about 0.2% by weight of the emulsion;
methylparaben, from about 0.1% to about 0.5% by weight of the emulsion;
propylparaben, from about 0.05% to about 0.2% by weight of the emulsion;
sodium hydroxide, from about 0.005% to about 0.05% by weight of the emulsion; and
sodium phosphate monobasic, from about 0.1% to about 1.5% by weight of the emulsion.

In certain embodiments, the invention relates to an emulsion, consisting of:
cetearyl alcohol, from about 1% to about 3% by weight of the emulsion;
emulsifying wax, from about 1% to about 3% by weight of the emulsion;
steareth-10, from about 0.3% to about 1.1% by weight of the emulsion;
dimethicone, from about 0.5% to about 1.5% by weight of the emulsion;
water, from about 65% to about 90% by weight of the emulsion;
clindamycin phosphate, from about 0.5% to about 1.8% by weight of the emulsion;
glycerol, from about 6% to about 18% by weight of the emulsion;
disodium EDTA, from about 0.05% to about 0.2% by weight of the emulsion;
methylparaben, from about 0.1% to about 0.5% by weight of the emulsion;
propylparaben, from about 0.05% to about 0.2% by weight of the emulsion;
sodium hydroxide, from about 0.005% to about 0.05% by weight of the emulsion; and
sodium phosphate monobasic, from about 0.1% to about 1.5% by weight of the emulsion.

In certain embodiments, the invention relates to an emulsion, comprising:
cetearyl alcohol, in about 2.0% by weight of the emulsion;
emulsifying wax, in about 2.0% by weight of the emulsion;
steareth-10, in about 0.8% by weight of the emulsion;
dimethicone, in about 1.0% by weight of the emulsion;
water, in about 79.7% by weight of the emulsion;
clindamycin phosphate, in about 1.2% by weight of the emulsion;
glycerol, in about 12.5% by weight of the emulsion;
disodium EDTA, in about 0.1% by weight of the emulsion;
methylparaben, in about 0.3% by weight of the emulsion;
propylparaben, in about 0.1% by weight of the emulsion;
sodium hydroxide, in about 0.01% by weight of the emulsion; and
sodium phosphate monobasic, in about 0.3% by weight of the emulsion.

In certain embodiments, the invention relates to an emulsion, consisting essentially of:
cetearyl alcohol, in about 2.0% by weight of the emulsion;
emulsifying wax, in about 2.0% by weight of the emulsion;
steareth-10, in about 0.8% by weight of the emulsion;
dimethicone, in about 1.0% by weight of the emulsion;
water, in about 79.7% by weight of the emulsion;
clindamycin phosphate, in about 1.2% by weight of the emulsion;
glycerol, in about 12.5% by weight of the emulsion;
disodium EDTA, in about 0.1% by weight of the emulsion;
methylparaben, in about 0.3% by weight of the emulsion;
propylparaben, in about 0.1% by weight of the emulsion;
sodium hydroxide, in about 0.01% by weight of the emulsion; and
sodium phosphate monobasic, in about 0.3% by weight of the emulsion.

In certain embodiments, the invention relates to an emulsion, consisting of:
cetearyl alcohol, in about 2.0% by weight of the emulsion;
emulsifying wax, in about 2.0% by weight of the emulsion;
steareth-10, in about 0.8% by weight of the emulsion;
dimethicone, in about 1.0% by weight of the emulsion;
water, in about 79.7% by weight of the emulsion;
clindamycin phosphate, in about 1.2% by weight of the emulsion;
glycerol, in about 12.5% by weight of the emulsion;
disodium EDTA, in about 0.1% by weight of the emulsion;
methylparaben, in about 0.3% by weight of the emulsion;
propylparaben, in about 0.1% by weight of the emulsion;
sodium hydroxide, in about 0.01% by weight of the emulsion; and
sodium phosphate monobasic, in about 0.3% by weight of the emulsion.

In certain embodiments, the invention relates to an emulsion, comprising:
cetearyl alcohol, in about 2.0% by weight of the emulsion;
emulsifying wax, in about 2.0% by weight of the emulsion;
steareth-10, in about 0.8% by weight of the emulsion;
dimethicone, in about 1.0% by weight of the emulsion;
water, in about 79.0% by weight of the emulsion;
clindamycin phosphate, in about 1.2% by weight of the emulsion;
glycerol, in about 12.5% by weight of the emulsion;
disodium EDTA, in about 0.1% by weight of the emulsion;
methylparaben, in about 0.3% by weight of the emulsion;
propylparaben, in about 0.1% by weight of the emulsion;
sodium hydroxide, in about 0.03% by weight of the emulsion; and
sodium phosphate monobasic, in about 1.0% by weight of the emulsion.

In certain embodiments, the invention relates to an emulsion, consisting essentially of:
cetearyl alcohol, in about 2.0% by weight of the emulsion;
emulsifying wax, in about 2.0% by weight of the emulsion;
steareth-10, in about 0.8% by weight of the emulsion;
dimethicone, in about 1.0% by weight of the emulsion;
water, in about 79.0% by weight of the emulsion;
clindamycin phosphate, in about 1.2% by weight of the emulsion;
glycerol, in about 12.5% by weight of the emulsion;
disodium EDTA, in about 0.1% by weight of the emulsion;
methylparaben, in about 0.3% by weight of the emulsion;
propylparaben, in about 0.1% by weight of the emulsion;
sodium hydroxide, in about 0.03% by weight of the emulsion; and
sodium phosphate monobasic, in about 1.0% by weight of the emulsion.

In certain embodiments, the invention relates to an emulsion, consisting of:
cetearyl alcohol, in about 2.0% by weight of the emulsion;
emulsifying wax, in about 2.0% by weight of the emulsion;
steareth-10, in about 0.8% by weight of the emulsion;
dimethicone, in about 1.0% by weight of the emulsion;
water, in about 79.0% by weight of the emulsion;
clindamycin phosphate, in about 1.2% by weight of the emulsion;
glycerol, in about 12.5% by weight of the emulsion;
disodium EDTA, in about 0.1% by weight of the emulsion;
methylparaben, in about 0.3% by weight of the emulsion;
propylparaben, in about 0.1% by weight of the emulsion;
sodium hydroxide, in about 0.03% by weight of the emulsion; and
sodium phosphate monobasic, in about 1.0% by weight of the emulsion.

Exemplary Components of the Oil Phase

As outlined above, in certain embodiments, the invention relates to an emulsion comprising an oil phase, wherein the oil phase comprises an emulsifier or surfactant, and a first moisturizer or first emollient. The components described below may be present in the oil phase of any one of the aforementioned emulsions.

In certain embodiments, the invention relates to any one of the aforementioned emulsions, wherein the emulsifier or surfactant is selected from the group consisting of: polysorbate 20, polysorbate 40, polysorbate 60, polysorbate 80, steareth-10, sodium dodecyl sulfate, lauryl dimethyl amine oxide, cetyltrimethylammonium bromide, polyethoxylated alcohols, polyoxyethylene sorbitan, octoxynol, N,N-dimethyldodecylamine-N-oxide, hexadecyltrimethylammonium bromide, polyoxyl 10 lauryl ether, sodium deoxycholate, sodium cholate, polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate, ceteareth-10 phosphate, methylbenzethonium chloride, behentrimonium methosulfate-cetearyl alcohol, emulsifying wax, polyoxyethylene oleyl ether, PEG-40 stearate, cetostearyl alcohol, ceteareth-12, ceteareth-20, ceteareth-30, ceteareth alcohol, glyceryl stearate, PEG-100 stearate, glyceryl stearate, PEG-100 stearate, steareth-2, steareth-20, stearamidopropyl dimethylamine, and behentrimonium methosulfate, and combinations/mixtures thereof.

In certain embodiments, the invention relates to any one of the aforementioned emulsions, wherein the emulsifier or surfactant is selected from the group consisting of cetearyl alcohol, emulsifying wax, and steareth-10, and combinations/mixtures thereof.

In certain embodiments, the invention relates to any one of the aforementioned emulsions, wherein the emulsifier or surfactant is present in an amount from about 0.5% to about 15% by weight of the emulsion. In certain embodiments, the emulsifier or surfactant is present in an amount from about 2% to about 8% by weight of the emulsion. In certain embodiments, the emulsifier or surfactant is present in an amount of about 2%, about 2.5%, about 3%, about 3.5%, about 4%, about 4.5%, about 5%, about 5.5%, about 6%, about 6.5%, about 7%, about 7.5%, or about 8% by weight of the emulsion.

In certain embodiments, the invention relates to any one of the aforementioned emulsions, wherein the emulsifier or surfactant comprises cetostearyl alcohol (cetearyl alcohol). In certain embodiments, the cetostearyl alcohol is present in an amount from about 0.2% to about 6% by weight of the emulsion. In certain embodiments, the cetostearyl alcohol is present in an amount from about 1.0% to about 3.0% by weight of the emulsion. In certain embodiments, cetostearyl alcohol is present in about 1.0%, about 1.5%, about 2.0%, about 2.5%, or about 3.0% by weight of the emulsion.

In certain embodiments, the invention relates to any one of the aforementioned emulsions, wherein the emulsifier or surfactant comprises emulsifying wax. In certain embodiments, the emulsifying wax is present in an amount from about 0.2% to about 6% by weight of the emulsion. In certain embodiments, the emulsifying wax is present in an amount from about 1.0% to about 3.0% by weight of the emulsion. In certain embodiments, emulsifying wax is present in about 1.0%, about 1.5%, about 2.0%, about 2.5%, or about 3.0% by weight of the emulsion.

In certain embodiments, the invention relates to any one of the aforementioned emulsions, wherein the emulsifier or surfactant comprises steareth-10. In certain embodiments, the steareth-10 is present in an amount from about 0.1% to about 2.3% by weight of the emulsion. In certain embodiments, the steareth-10 is present in an amount from about 0.3% to about 1.1% by weight of the emulsion. In certain embodiments, steareth-10 is present in about 0.3%, about 0.4%, about 0.5%, about 0.6%, about 0.7%, about 0.8%, about 0.9%, about 1.0%, or about 1.1% by weight of the emulsion.

In certain embodiments, the invention relates to any one of the aforementioned emulsions, wherein the first moisturizer or first emollient is selected from the group consisting of petrolatum, lactic acid, glycerol, propylene glycol, butylene glycol, sodium PCA, sodium hyaluronate, CARBOWAX® 200 polyethylene glycols, CARBOWAX® 400 polyethylene glycols, CARBOWAX® 800 polyethylene glycols, cetyl palmitate, glycerol, PPG-15 stearyl ether, lanolin alcohol, lanolin, lanolin derivatives, cholesterol, isostearyl neopentanoate, octyl stearate, mineral oil, isocetyl stearate, myristyl myristate, octyl dodecanol, 2-ethylhexyl palmitate, dimethicone, phenyl trimethicone, cyclomethicone, $C_{12}$-$C_{15}$ alkyl benzoates, dimethiconol, propylene glycol, *Theobroma grandiflorum* seed butter, ceramide 2, ceramide 3, hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, and dicaprylate/dicaprate, and combinations/mixtures thereof.

In certain embodiments, the invention relates to any one of the aforementioned emulsions, wherein the first moisturizer or first emollient is selected from the group consisting of dimethicone, cyclomethicone, white petrolatum, and combinations/mixtures thereof.

In certain embodiments, the invention relates to any one of the aforementioned emulsions, wherein the first moisturizer or first emollient is present in an amount from about 0.2% to about 12% by weight of the emulsion. In certain embodiments, the first moisturizer or first emollient is present in an amount from about 0.5% to about 1.5% by weight of the emulsion. In certain embodiments, the first moisturizer or first emollient is present in an amount of about 0.5%, about 0.6%, about 0.7%, about 0.8%, about 0.9%, about 1.0%, about 1.1%, about 1.2%, about 1.3%, about 1.4%, or about 1.5% by weight of the emulsion.

In certain embodiments, the invention relates to any one of the aforementioned emulsions, wherein the first moisturizer or first emollient comprises dimethicone. In certain embodiments, the dimethicone is present in an amount from about 0.2% to about 3% by weight of the emulsion. In certain embodiments, the dimethicone is present in an amount from about 0.5% to about 1.5% by weight of the emulsion. In certain embodiments, the dimethicone is present in about 0.5%, about 0.6%, about 0.7%, about 0.8%, about 0.9%, about 1.0%, about 1.1%, about 1.2%, about 1.3%, about 1.4%, or about 1.5% by weight of the emulsion.

In certain embodiments, the invention relates to any one of the aforementioned emulsions, wherein the first moisturizer or first emollient comprises cyclomethicone. In certain embodiments, the cyclomethicone is present in an amount from about 2.5% to about 7.5% by weight of the emulsion. In certain embodiments, the cyclomethicone is present in an amount from about 3.5% to about 6.5% by weight of the emulsion. In certain embodiments, the cyclomethicone is present in about 3.5%, about 4.0%, about 4.5%, about 5.0%, about 5.5%, about 6.0%, or about 6.5% by weight of the emulsion.

In certain embodiments, the invention relates to any one of the aforementioned emulsions, wherein the first moisturizer or first emollient comprises white petrolatum. In certain embodiments, the white petrolatum is present in an amount from about 0.5% to about 1.5% by weight of the emulsion. In certain embodiments, the white petrolatum is present in an amount from about 0.7% to about 1.3% by weight of the emulsion. In certain embodiments, the white petrolatum is present in about 0.7%, about 0.8%, about 0.9%, about 1.0%, about 1.2%, or about 1.3% by weight of the emulsion.

In certain embodiments, the invention relates to any one of the aforementioned emulsions, further comprising a second antioxidant or second preservative. In certain embodiments, the second antioxidant or second preservative is selected from the group consisting of imidazolidinyl urea, diazolidinyl urea, phenoxyethanol, sodium methyl paraben, methylparaben, ethylparaben, propylparaben, potassium sorbate, sodium benzoate, sorbic acid, benzoic acid, formaldehyde, citric acid, sodium citrate, chlorine dioxide, benzalkonium chloride, benzethonium chloride, cetrimide, dequalinium chloride, cetylpyridinium chloride, phenylmercuric nitrate, phenylmercuric acetate, thimerosal, piroctone olamine, *Vitis vinifera* seed oil, chlorobutanol, dichlorobenzyl alcohol, phenylethyl alcohol, benzyl alcohol, ascorbic acid, sodium bisulfite, butylated hydroxytoluene, butylated hydroxyanisole, α-tocopherol, tocopheryl acetate, sodium ascorbate/ascorbic acid, ascorbyl palmitate, propyl gallate, disodium EDTA, citric acid, and sodium citrate, and combinations/mixtures thereof.

In certain embodiments, the invention relates to any one of the aforementioned emulsions, wherein the second antioxidant or second preservative comprises tocopheryl acetate.

In certain embodiments, the invention relates to any one of the aforementioned emulsions, wherein the second antioxidant or second preservative is present in an amount from about 0.05% to about 0.2% by weight of the emulsion. In certain embodiments, the second antioxidant or second preservative is present in an amount from about 0.08% to about 0.2% by weight of the emulsion. In certain embodiments, the second antioxidant or second preservative is present in an amount of about 0.08%, about 0.09%, about 0.1%, about 0.11%, or about 0.12% by weight of the emulsion.

In certain embodiments, the invention relates to any one of the aforementioned emulsions, wherein the second antioxidant or second preservative comprises tocopheryl acetate. In certain embodiments, the tocopheryl acetate is present in an amount from about 0.05% to about 0.2% by weight of the emulsion. In certain embodiments, the tocopheryl acetate is present in an amount from about 0.08% to about 0.2% by weight of the emulsion. In certain embodiments, tocopheryl acetate is present in about 0.08%, about 0.09%, about 0.1%, about 0.11%, or about 0.12% by weight of the emulsion.

Exemplary Components of the Aqueous Phase

As outlined above, in certain embodiments, the invention relates to an emulsion comprising an aqueous phase, wherein the aqueous phase comprises water, an antibiotic, a second moisturizer or second emollient, an antioxidant or preservative, a pH adjuster, and a buffer salt. The components described below may be present in the aqueous phase of any one of the aforementioned emulsions.

In certain embodiments, the invention relates to any one of the aforementioned emulsions, wherein water is present in an amount about 65% to about 90% by weight of the emulsion. In certain embodiments, water is present in an amount from about 70% to about 85% by weight of the emulsion. In certain embodiments, water is present in an amount of about 70%, about 72%, about 74%, about 76%, about 78%, about 80%, about 82%, or about 84% by weight of the emulsion.

In certain embodiments, the invention relates to any one of the aforementioned emulsions, wherein the antibiotic is an antibacterial or an antifungal. In certain embodiments, the invention relates to any one of the aforementioned emulsions, wherein the antibiotic is selected from the group consisting of amanfadine (e.g., amanfadine hydrochloride, amanfadine sulfate), amikacin (e.g., amikacin sulfate), anidulafungin, azelaic acid, benzoyl peroxide, butenafine, capreomycin, chlorhexidine (e.g., chlorhexidine gluconate, chlorhexidine hydrochloride), chlortetracycline (e.g., chlortetracycline hydrochloride), ciclopirox, ciprofloxacin, clindamycin (e.g., clindamycin phosphate, clindamycin hydrochloride), clotrimazole, doxycycline (e.g., doxycycline hydrochloride), econazole, erythromycin (e.g., erythromycin estolate, erythromycin stearate), ethambutol (e.g., ethambutol hydrochloride), ethyl acetate, famesol, flavinoids, gentamicin (e.g., gentamicin sulfate), itraconazole, kanamycin (e.g., kanamycin sulfate), ketoconazole, beta-lactam drugs, lanoconazole, lineomycin (e.g., lineomycin hydrochloride), meclocycline, methacycline (e.g., methacycline hydrochloride), methenamine (e.g., methenamine hippurate, methenamine mandelate), metronidazole (e.g., metronidazole hydrochloride), micafungin, miconazole (e.g., miconazole hydrochloride), minocycline (e.g., minocycline hydrochloride), naftifine, neomycin (e.g., neomycin sulfate), netilmicin (e.g., netilmicin sulfate), norfloxacin, nystatin, octopirox, oxiconazole, oxytetracycline (e.g., oxytetracycline hydrochloride), paromomycin (e.g., paromomycin sulfate), pentamidine (e.g., pentamidine hydrochloride), phenoxy ethanol, phenoxy propanol, quinolone drugs, streptomycin (e.g., streptomycin sulfate), sulconazole, terbinafine, tetracycline (e.g., tetracycline hydrochloride), tobramycin (e.g., tobramycin sulfate), tolnaftate, triclosan, undecylinic acid, voriconazole, zinc, and combinations/mixtures thereof.

In certain embodiments, the invention relates to any one of the aforementioned emulsions, wherein the antibiotic comprises clindamycin. In certain embodiments, the antibiotic comprises clindamycin phosphate.

In certain embodiments, the invention relates to any one of the aforementioned emulsions, wherein the antibiotic is present in an amount from about 0.5% to about 1.8% by weight of the emulsion. In certain embodiments, the antibiotic is present in an amount from about 0.7% to about 1.6% by weight of the emulsion. In certain embodiments, the antibiotic is present in an amount of about 0.7%, about 0.8%, about 0.9%, about 1.0%, about 1.1%, about 1.2%, about 1.3%, about 1.4%, about 1.5%, or about 1.6% by weight of the emulsion.

In certain embodiments, the invention relates to any one of the aforementioned emulsions, wherein the antibiotic comprises clindamycin phosphate. In certain embodiments, the clindamycin phosphate is present in an amount from about 0.5% to about 1.8% by weight of the emulsion. In certain embodiments, the clindamycin phosphate is present in an amount from about 0.7% to about 1.6% by weight of the emulsion. In certain embodiments, the clindamycin phosphate is present in an amount of about 0.7%, about 0.8%, about 0.9%, about 1.0%, about 1.1%, about 1.2%, about 1.3%, about 1.4%, about 1.5%, or about 1.6% by weight of the emulsion.

In certain embodiments, the invention relates to any one of the aforementioned emulsions, further comprising a second antibiotic. In certain embodiments, the second antibiotic is benzoyl peroxide. In certain embodiments, the benzoyl peroxide is present in an amount from about 1.0% to about 6.0% by weight of the emulsion.

In certain embodiments, the invention relates to any one of the aforementioned emulsions, wherein the second moisturizer or second emollient is selected from the group consisting of petrolatum, lactic acid, glycerol, propylene glycol, butylene glycol, sodium PCA, sodium hyaluronate, CARBOWAX® 200 polyethylene glycols, CARBOWAX® 400 polyethylene glycols, CARBOWAX® 800 polyethylene glycols, cetyl palmitate, glycerol, PPG-15 stearyl ether, lanolin alcohol, lanolin, lanolin derivatives, cholesterol, isostearyl neopentanoate, octyl stearate, mineral oil, isocetyl stearate, myristyl myristate, octyl dodecanol, 2-ethylhexyl palmitate, dimethicone, phenyl trimethicone, cyclomethicone, $C_{12}$-$C_{15}$ alkyl benzoates, dimethiconol, propylene glycol, *Theobroma grandiflorum* seed butter, ceramide 2, ceramide 3, hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, and dicaprylate/dicaprate, and combinations/mixtures thereof.

In certain embodiments, the invention relates to any one of the aforementioned emulsions, wherein the second moisturizer or second emollient is selected from the group consisting of propylene glycol, glycerol, and combinations/mixtures thereof.

In certain embodiments, the invention relates to any one of the aforementioned emulsions, wherein the second moisturizer or second emollient is present in an amount from about 2.5% to about 37% by weight of the emulsion. In certain embodiments, the second moisturizer or second emollient is present in an amount from about 5% to about 20% by weight of the emulsion. In certain embodiments, the second moisturizer or second emollient is present in an amount of about 5%, about 6%, about 7%, about 8%, about 9%, about 10%, about 11%, about 12%, about 13%, about 14%, about 15%, about 16%, about 17%, about 18%, about 19%, or about 20% by weight of the emulsion.

In certain embodiments, the invention relates to any one of the aforementioned emulsions, wherein the second moisturizer or second emollient comprises glycerol. In certain embodiments, the glycerol is present in an amount from about 2.5% to about 30% by weight of the emulsion. In certain embodiments, the glycerol is present in an amount from about 6% to about 18% by weight of the emulsion. In certain embodiments, the glycerol is present in about 6%, about 7%, about 8%, about 9%, about 10%, about 11%, about 12%, about 13%, about 14%, about 15%, about 16%, about 17%, or about 18% by weight of the emulsion.

In certain embodiments, the invention relates to any one of the aforementioned emulsions, wherein the second moisturizer or second emollient comprises propylene glycol. In certain embodiments, the propylene glycol is present in an amount from about 2.5% to about 7.5% by weight of the emulsion. In certain embodiments, the propylene glycol is present in an amount from about 3% to about 7% by weight of the emulsion. In certain embodiments, the propylene glycol is present in about 3.0%, about 3.5%, about 4.0%, about 4.5%, about 5.0%, about 5.5%, about 6.0%, about 6.5%, or about 7.0% by weight of the emulsion.

In certain embodiments, the invention relates to any one of the aforementioned emulsions, wherein the antioxidant or preservative is selected from the group consisting of imidazolidinyl urea, diazolidinyl urea, phenoxyethanol, sodium methyl paraben, methylparaben, ethylparaben, propylparaben, potassium sorbate, sodium benzoate, sorbic acid, benzoic acid, formaldehyde, citric acid, sodium citrate, chlorine dioxide, benzalkonium chloride, benzethonium chloride, cetrimide, dequalinium chloride, cetylpyridinium chloride, phenylmercuric nitrate, phenylmercuric acetate, thimerosal, piroctone olamine, *Vitis vinifera* seed oil, chlorobutanol, dichlorobenzyl alcohol, phenylethyl alcohol, benzyl alcohol, ascorbic acid, sodium bisulfite, butylated hydroxytoluene, butylated hydroxyanisole, α-tocopherol, tocopheryl acetate, sodium ascorbate/ascorbic acid, ascorbyl palmitate, propyl gallate, disodium EDTA, citric acid, and sodium citrate, and combinations/mixtures thereof.

In certain embodiments, the invention relates to any one of the aforementioned emulsions, wherein the antioxidant or preservative is selected from the group consisting of disodium EDTA, methylparaben, propylparaben and combinations/mixtures thereof.

In certain embodiments, the invention relates to any one of the aforementioned emulsions, wherein the antioxidant or preservative is present in an amount from about 0.05% to about 0.8% by weight of the emulsion. In certain embodiments, the antioxidant or preservative is present in an amount from about 0.1% to about 0.7% by weight of the emulsion. In certain embodiments, the antioxidant or preservative is present in an amount of about 0.1%, about 0.2%, about 0.3%, about 0.4%, about 0.5%, about 0.6%, or about 0.7% by weight of the emulsion.

In certain embodiments, the invention relates to any one of the aforementioned emulsions, wherein the antioxidant or preservative comprises disodium EDTA. In certain embodiments, the disodium EDTA is present in an amount from about 0.05% to about 0.2% by weight of the emulsion. In certain embodiments, the disodium EDTA is present in an amount from about 0.08% to about 0.12% by weight of the emulsion. In certain embodiments, the disodium EDTA is present in about 0.08%, about 0.09%, about 0.1%, about 0.11%, or about 0.12% by weight of the emulsion.

In certain embodiments, the invention relates to any one of the aforementioned emulsions, wherein the antioxidant or preservative comprises methylparaben. In certain embodiments, the methylparaben is present in an amount from about 0.1% to about 0.5% by weight of the emulsion. In certain embodiments, the methylparaben is present in an amount from about 0.2% to about 0.4% by weight of the emulsion. In certain embodiments, the methylparaben is present in about 0.2%, about 0.25%, about 0.3%, about 0.35%, or about 0.4% by weight of the emulsion.

In certain embodiments, the invention relates to any one of the aforementioned emulsions, wherein the antioxidant or preservative propylparaben. In certain embodiments, the propylparaben is present in an amount from about 0.05% to about 0.2% by weight of the emulsion. In certain embodiments, the propylparaben is present in an amount from about 0.08% to about 0.12% by weight of the emulsion. In certain embodiments, the propylparaben is present in about 0.08%, about 0.09%, about 0.1%, about 0.11%, or about 0.12% by weight of the emulsion.

In certain embodiments, the invention relates to any one of the aforementioned emulsions, wherein the pH adjuster is selected from the group consisting of citric acid, sodium hydroxide, and sodium phosphate, and combinations/mixtures thereof.

In certain embodiments, the invention relates to any one of the aforementioned emulsions, wherein the pH adjuster comprises sodium hydroxide.

In certain embodiments, the invention relates to any one of the aforementioned emulsions, wherein the pH of the emulsion is from about 4.0 to about 7.5. In certain embodiments, the invention relates to any one of the aforementioned emulsions or compositions, wherein the pH of the emulsion is from about 4.5 to about 6.5. In certain embodiments, the invention relates to any one of the aforementioned emulsions or compositions, wherein the pH of the emulsion is about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0.

In certain embodiments, the invention relates to any one of the aforementioned emulsions, wherein the buffer salt is selected from the group consisting of sodium phosphate monobasic, sodium phosphate dibasic, sodium phosphate tribasic, potassium phosphate monobasic, potassium phosphate dibasic, and potassium phosphate tribasic.

In certain embodiments, the invention relates to any one of the aforementioned emulsions, wherein the buffer salt is comprises sodium phosphate monobasic.

In certain embodiments, the invention relates to any one of the aforementioned emulsions, wherein the buffer salt is present in an amount from about 0.1% to about 1.5% by weight of the emulsion. In certain embodiments, the buffer salt is present in an amount from about 0.2% to about 1.4% by weight of the emulsion. In certain embodiments, the buffer salt is present in an amount of about 0.2%, about 0.3%, about 0.4%, about 0.5%, about 0.6%, about 0.7%, about 0.8%, about 0.9%, about 1.0%, about 1.1%, about 1.2%, about 1.3%, or about 1.4% by weight of the emulsion.

Exemplary Compositions of the Invention

In certain embodiments, the invention relates to a composition, comprising:
 any one of the aforementioned emulsions;
 a propellant; and
 a purge gas.

In certain embodiments, the invention relates to a composition, consisting essentially of:
 any one of the aforementioned emulsions;
 a propellant; and
 a purge gas.

In certain embodiments, the invention relates to a composition, consisting of:
 any one of the aforementioned emulsions;
 a propellant; and
 a purge gas.

Exemplary Propellants

As outlined above, in certain embodiments, the invention relates to a composition comprising an emulsion, a propellant, and a purge gas. The propellants described below may be present in any one of the aforementioned compositions.

In certain embodiments, the invention relates to any one of the aforementioned compositions, wherein the propellant is selected from the group consisting of 1,1,1,2-tetrafluoroethane, 1,1,1,2,3,3,3-heptafluoropropane, and combinations/mixtures thereof.

In certain embodiments, the invention relates to any one of the aforementioned compositions, wherein the propellant is present in an amount from about 3% to about 20% by weight of the composition. In certain embodiments, the invention relates to any one of the aforementioned compositions, wherein the propellant is present in an amount from about 5% to about 18% by weight of the composition. In certain embodiments, the invention relates to any one of the aforementioned compositions, wherein the propellant is about 5%, about 6%, about 7%, about 8%, about 9%, about 10%, about 11%, about 12%, about 13%, about 14%, about 15%, about 16%, about 17%, or about 18% by weight of the composition.

Exemplary Purge Gases

As outlined above, in certain embodiments, the invention relates to a composition comprising an emulsion, a propellant, and a purge gas. The purge gases described below may be present in any one of the aforementioned compositions.

In certain embodiments, the invention relates to any one of the aforementioned compositions, wherein the purge gas is selected from the group consisting of nitrogen and argon. In certain embodiments, the invention relates to any one of the aforementioned compositions, wherein the purge gas is argon.

In certain embodiments, the invention relates to any one of the aforementioned compositions, wherein the purge gas is present in an amount from about 0.4% to about 6% by weight of the composition. In certain embodiments, the invention relates to any one of the aforementioned compositions, wherein the purge gas is present in an amount from about 0.8% to about 5% by weight of the composition. In certain embodiments, the invention relates to any one of the aforementioned compositions, wherein the purge gas is about 0.8%, about 1%, about 1.2%, about 1.4%, about 1.6%, about 1.8%, about 2%, about 2.2%, about 2.5%, about 2.6%, about 2.8%, about 3%, about 3.2%, about 3.4%, about 3.6%, about 3.8%, about 4%, about 4.2%, about 4.4%, about 4.6%, about 4.8% or about 5% by weight of the composition.

Exemplary Properties of Emulsions and Compositions of the Invention

In certain embodiments, the invention relates to any one of the aforementioned emulsions or compositions, wherein the emulsion or composition is non-irritating when applied to the skin of a subject.

In certain embodiments, the invention relates to any one of the aforementioned emulsions or compositions, wherein the emulsion or composition is well-tolerated when applied to the skin of a subject.

In certain embodiments, the invention relates to any one of the aforementioned emulsions or compositions, wherein the emulsion or composition is non-cytotoxic when applied to the skin of a subject.

In certain embodiments, the invention relates to any one of the aforementioned emulsions or compositions, wherein the emulsion or composition is weakly sensitizing when applied to the skin of a subject.

In certain embodiments, the invention relates to any one of the aforementioned emulsions or compositions, wherein the emulsion or composition is non-sensitizing when applied to the skin of a subject.

In certain embodiments, the invention relates to any one of the aforementioned emulsions or compositions, wherein the emulsion or composition does not produce edema or erythema when applied to the skin of a subject.

In certain embodiments, the invention relates to any one of the aforementioned emulsions or compositions, wherein the emulsion or composition is moisturizing when applied to the skin of a subject.

In certain embodiments, the invention relates to any one of the aforementioned emulsions or compositions, wherein the emulsion or composition increases hydration when applied to the skin of a subject.

In certain embodiments, the invention relates to any one of the aforementioned emulsions or compositions, wherein the emulsion or composition reduces transepidermal water loss when applied to the skin of a subject.

In certain embodiments, the invention relates to any one of the aforementioned emulsions or compositions, wherein the emulsion or composition forms a foam when expelled from an aerosol container. In certain embodiments, the foam is time-stable. In certain embodiments, the density of the foam is from about 0.05 to about 0.5 g/cm$^3$. In certain embodiments, the invention relates to any one of the aforementioned compositions, wherein the composition is easily shaken in an aerosol container. In certain embodiments, the invention relates to any one of the aforementioned compositions, wherein the composition is easily dispensed from an aerosol container.

Exemplary Emulsions and Compositions of the Invention for Particular Uses

In certain embodiments, the invention relates to any one of the aforementioned emulsions or compositions for use in the treatment of acne vulgaris.

In certain embodiments, the invention relates to any one of the aforementioned emulsions or compositions for use in the treatment of comedonal acne vulgaris or papulo-pustular acne vulgaris.

In certain embodiments, the invention relates to any one of the aforementioned emulsions or compositions for use in the treatment of acne vulgaris, wherein the acne vulgaris is associated with non-inflammatory lesions or inflammatory lesions.

In certain embodiments, the invention relates to any one of the aforementioned emulsions or compositions for use in the treatment of acne vulgaris of the face, chest, or back.

In certain embodiments, the invention relates to any one of the aforementioned emulsions or compositions for use in the treatment of acne vulgaris, wherein the emulsion or composition is formulated for topical application once daily or twice daily.

Exemplary Methods of Use

In certain embodiments, the invention relates to a method of treating acne vulgaris, comprising the step of applying to an affected area of a subject in need thereof a therapeutically-effective amount of any one of the aforementioned emulsions or compositions.

In certain embodiments, the invention relates to any one of the aforementioned methods, wherein the acne vulgaris is comedonal or papulo-pustular.

In certain embodiments, the invention relates to any one of the aforementioned methods, wherein the subject presents with non-inflammatory lesions or inflammatory lesions.

In certain embodiments, the invention relates to any one of the aforementioned methods, wherein the acne vulgaris is mild, moderate, or severe. In certain embodiments, the invention relates to any one of the aforementioned methods, wherein the acne vulgaris is mild or moderate.

In certain embodiments, the invention relates to any one of the aforementioned methods, wherein the affected area is the face, chest, or back.

In certain embodiments, the invention relates to any one of the aforementioned methods, wherein the emulsion or composition is applied once daily or twice daily.

EXEMPLIFICATION

Example 1

Compositions and Method of Manufacture

An example product concentrate (NB216-2) was manufactured by the procedure outlined below:

Step 1: Oil Phase Preparation
1. Charge emulsifying wax, steareth-10, cetearyl alcohol and dimethicone into a Stainless Steel tank and heat to about 75-about 80° C.

Step 2: Aqueous Phase Preparation
1. Charge purified water (Part A) and glycerin into a Stainless Steel tank and heat to about 75-about 80° C.
2. Charge and dissolve methyl paraben, propyl paraben, disodium EDTA and sodium phosphate monobasic while mixing.
3. Continue mixing until a clear solution is obtained while maintaining a temperature of about 75-about 80° C.

Step 3: Drug Phase Preparation
1. Charge purified water (Part B) into stainless steel tank
2. Dissolve Clindamycin Phosphate while mixing Step 4: Final Emulsion Formation
1. Add Step 1 to Step 2 while high-shear mixing at about 75-about 80° C.
2. Cool the emulsion with an outside cold-water jacket to about 45-about 50° C. while high-shear mixing.
3. Discontinue high-shear mixing. Start low-shear mixing and continue cooling with cold-water jacket to form the vehicle emulsion.

4. When the temperature of the vehicle emulsion is about 37° C., add Step 3 and continue mixing until uniform.
5. Cool to about 27-about 32° C. Adjust to final pH with Sodium Hydroxide and final volume with DI water. Mix until uniform.

Following manufacturing of the Product Concentrate, the finished Product Concentrate was filled into aerosol cans as outlined below.

1. Aerosol cans are cleaned with compressed air and vacuum.
2. Product Concentrate is filled into cans.
3. Valves are placed onto the cans.
4. Cans are crimped and hydrofluorocarbon propellant is charged.
5. The aerosol can valve and dip-tube is purged with argon gas.

Propellant concentrations range from 8-15% by weight of packaged product, argon concentrations range from 0.8-4.0% by weight of packaged product.

Example 2

Stability

To examine the stability of clindamycin phosphate dissolved in various liquids, solutions of clindamycin phosphate were prepared and incubated at 20° C. for about 2 months. Contrary to expectation, it was found that the rate of hydrolysis of clindamycin phosphate dissolved in buffer was between 30-60-fold lower than the rate of clindamcyin phosphate hydrolysis in purified water. As expected, the rate of hydrolysis was lowest in non-aqueous solution (FIG. 2).

Clindamycin phosphate compositions containing glycerin with and without buffer salts were prepared as described in Example 1. The percentage of hydrolyzed clindamycin phosphate was measured as a function of time. The results demonstrated lower amounts of clindamycin phosphate hydrolysis in buffer-containing compositions during incubation at both 25° C. and 40° C. (FIG. 3).

The rate of clindamycin phosphate hydrolysis was calculated for compositions containing glycerin with and without buffer salts. In the presence or absence of buffer salts the rate of clindamycin phosphate hydrolysis was lower than the rate of hydrolysis of clindamycin phosphate dissolved in water. Compositions containing both glycerin and buffer salts demonstrated lower rates of clindamycin phosphate hydrolysis than did compositions containing buffer alone (FIG. 4).

Example 3

Product Tolerability (Repeat Dose Dermal Toxicity)

A 90-day Repeat Dose Dermal Toxicity Study of NB216-2 was carried on in Gottingen Minipigs. Six (6) male and six (6) female minipigs between 5 and 6 months of age were used. Prior to beginning dosing, the pigs had their backs washed and then shaved free of hair. Four rectangular sites (4×4-cm) were marked with indelible ink approximately 8 cm from the midline and approximately 6 cm apart on the back on each side of the midline. The test sites were shaved and the site markings refreshed as needed over the course of the study. Beginning on Day 1, and at approximately the same time each day thereafter, the test sites were dosed as shown below and the times of the daily dermal applications recorded.

Sites 1 (left and right): (most anterior) Control—49.6 mg applied once daily once in the morning.
Site 2 (left and right): NB216-2—49.6 mg applied once daily in the morning.
Site 3 (left and right): Mock treatment—once daily in the morning
Site 4 (left and right): (most posterior) NB216-2—49.6 mg applied twice daily in the morning and once in the afternoon, each application separated by a minimum of 5 hours.

The test sites received a thin uniform covering with NB216-2 or control article which were rubbed in. The test sites were left uncovered. Mock treatment included preparing the test sites and daily rubbing to simulate the procedure used to apply NB216-2 and control articles.

Application areas (all sites) were examined and graded in accordance with the score scale presented below (Magnusson and Kligman, 1969) once daily in the afternoon prior to the second application.

Score Scale
  0 No reaction
  ± Very slight, dispersed erythema
  1 Discrete (slight confluent) or moderate patchy erythema
  2 Moderate and confluent erythema
  3 Severe erythema and/or moderate to severe edema Also, the following dermal reactions were recorded, if they occurred: eschar, desquamation, blanching and/or evidence of necrosis. Other dermal findings, if present, were also noted.

On day 91, all study animals were sacrificed and a complete necropsy conducted under the direct supervision of a board certified veterinary pathologist. The tissues listed below were collected and placed in 10% neutral-buffered formalin:

All skin application sites
Non-application skin area[a]
a=A single non-application skin area of approximately equal size to the application area will be collected from the left shoulder region.

The collected tissues were examined microscopically for evidence of histopathologic changes associated with NB216-2 application.

In-Life Findings: All animals survived to necrospsy. There were no test article related effects on body weight. In addition there were no test article related clinical or dermal observations and no macroscopic findings on necropsy. It was found that NB216-2 was well tolerated by animals and had no test article-related findings.

Histopathological Findings: There was a slightly higher incidence of inflammation within the superficial dermis of NB216-2 treated sites under exaggerated dose conditions. Subacute dermal inflammation is commonly observed in minipigs. In the study, in addition to being observed in the test article-treated sites, inflammation was also observed at untreated, sham treated and vehicle treated sites and therefore was not considered adverse or dose limiting.

Prophetic Example 4

Skin Moisturization

The ability of the compositions of the invention to increase the hydration of treated skin was determined by means of corneometry. The measurement of the moisture content of the outermost layer of the skin (stratum corneum) by corneometry is a well-established technique widely used in the development of cosmetic, pharmaceutical and medical device products. Corneometry is based on capacitance measurement of a dielectric medium. Any change in the dielectric constant due to variation in skin surface hydration alters the capacitance of a precision measuring capacitor. One of the greatest advantages of the capacitance measurement method, compared to other measurement methods, is the fact that products applied to the skin only have minimal influence on the measurements. Due to the sensitivity of the method, the measurement can detect small changes in hydration level.

MoistureMeter SC (Delfin Technologies, Ltd.) Serial Number: SC4M277
Pre-moistened Towelettes
Indelible Marker/Marking Template
NB216-2
Evoclin Foam During the test session, both products will be tested against each other. Products will be applied using a paired comparison design between the left and right arms. As hair may interfere with the moisture measurements, test sites with the least amount of hair will be selected.

An exemplary procedure is outlined below:
1. Clean volar surfaces of both left and right arm with pre-moistened towelette and blot dry.
2. Mark 4.0×4.0-cm test areas using an indelible marker on volar surface of left and right arms.
3. Measure the moisture content of all sites five (5) times using the MoistureMeter SC.
4. To minimize interference with the probe select the most hairless area within the test site. Begin measurement by gently pressing the probe against the skin until three (3) green lights are showing. Measurement will commence when the unit beeps and will stop measuring after the second set of beeps. Record the measured skin moisture values.
5. Apply 400 mg of the each test article to the appropriate test area and completely rub-in.
6. At 30 minutes post application repeat steps 3 through 4.
7. At 1 hour post application repeat steps 3 through 4.
8. At 2 hours post application repeat steps 3 through 4.
9. At 4 hours post application repeat steps 3 through 4.
10. At 6 hours post application repeat steps 3 through 4.

Prophetic Example 5

Product Tolerability/Pharmacokinetics

An assessment of the safety and pharmacokinetics of NB216-2 was carried out in 30 male and female subjects 12 years or older suffering from mild to moderate acne vulgaris on the face and obvious acne on the chest and/or back. All subjects were instructed to shower up to 2 hours prior to arriving at the clinic. Subjects were provided with a mild soap to use during the study. Subjects were instructed not to shower or wash the treated areas at any other times during the day for the duration of the study.

In the study, four grams (4 g) of study medication was applied topically once daily over the face, chest, and back for 5 consecutive days. Subjects were required to return to the clinic at approximately the same time each day at which time study medication was applied by a member of the site staff to the face, chest, and back regardless of whether acne was present on the trunk. Serial blood samples for pharmacokinetic evaluation were collected on Day 1 at pre-dose and Day 5 at pre-dose and at 1.0, 2.0, 4.0, 6.0, 8.0, 10.0, and 12.0 hours post-dose. The incidence of treatment-emergent adverse events were assessed. Hematologic, biochemical, and urinalysis variables were assessed at screening and prior to discharge from the study.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A method of treating acne vulgaris, comprising the step of applying to an affected area of a subject in need thereof a therapeutically-effective amount of a composition, wherein the composition comprises
an emulsion, wherein the emulsion comprises:
cetostearyl alcohol, from about 1% to about 3% by weight of the emulsion;
emulsifying wax, from about 1% to about 3% by weight of the emulsion;
steareth-10, from about 0.3% to about 1.1% by weight of the emulsion;
dimethicone, from about 0.5% to about 1.5% by weight of the emulsion;
water, from about 65% to about 90% by weight of the emulsion;
clindamycin phosphate, from about 0.5% to about 1.8% by weight of the emulsion;
glycerol, from about 6% to about 18% by weight of the emulsion;
disodium EDTA, from about 0.05% to about 0.2% by weight of the emulsion;
methylparaben, from about 0.1% to about 0.5% by weight of the emulsion;
propylparaben, from about 0.05% to about 0.2% by weight of the emulsion;
sodium hydroxide, from about 0.005% to about 0.05% by weight of the emulsion; and
sodium phosphate monobasic, from about 0.1% to about 1.5% by weight of the emulsion;
a propellant; and
a purge gas.
2. The method of claim 1, wherein the acne vulgaris is comedonal, papulo-pustular, or nodular.
3. The method of claim 1, wherein the affected area is the face, chest, or back.
4. The method of claim 1, wherein the emulsion or composition is applied once daily or twice daily.
5. The method of claim 1, wherein the composition comprises:
an emulsion, wherein the emulsion comprises:
cetostearyl alcohol, in about 2.0% by weight of the emulsion;
emulsifying wax, in about 2.0% by weight of the emulsion;
steareth-10, in about 0.8% by weight of the emulsion;
dimethicone, in about 1.0% by weight of the emulsion;
water, in about 79.7% by weight of the emulsion;
clindamycin phosphate, in about 1.2% by weight of the emulsion;
glycerol, in about 12.5% by weight of the emulsion;
disodium EDTA, in about 0.1% by weight of the emulsion;
methylparaben, in about 0.3% by weight of the emulsion;

propylparaben, in about 0.1% by weight of the emulsion;

sodium hydroxide, in about 0.01% by weight of the emulsion; and sodium phosphate monobasic, in about 0.3% by weight of the emulsion;

a propellant; and a purge gas.

6. The method of claim 1, wherein the composition comprises:

an emulsion, wherein the emulsion comprises:

cetostearyl alcohol, in about 2.0% by weight of the emulsion;

emulsifying wax, in about 2.0% by weight of the emulsion;

steareth-10, in about 0.8% by weight of the emulsion;

dimethicone, in about 1.0% by weight of the emulsion;

water, in about 79.0% by weight of the emulsion;

clindamycin phosphate, in about 1.2% by weight of the emulsion;

glycerol, in about 12.5% by weight of the emulsion;

disodium EDTA, in about 0.1% by weight of the emulsion;

methylparaben, in about 0.3% by weight of the emulsion;

propylparaben, in about 0.1% by weight of the emulsion;

sodium hydroxide, in about 0.03% by weight of the emulsion; and sodium phosphate monobasic, in about 1.0% by weight of the emulsion;

a propellant; and a purge gas.

7. The method of claim 1, wherein the propellant is selected from the group consisting of 1,1,1,2-tetrafluoroethane, 1,1,1,2,3,3,3-heptafluoropropane, and combinations/mixtures thereof.

8. The method of claim 1, wherein the purge gas is selected from the group consisting of nitrogen and argon.

9. The method of claim 1, wherein the composition consists essentially of:

an emulsion, wherein the emulsion consists essentially of:

cetostearyl alcohol, from about 1% to about 3% by weight of the emulsion;

emulsifying wax, from about 1% to about 3% by weight of the emulsion;

steareth-10, from about 0.3% to about 1.1% by weight of the emulsion;

dimethicone, from about 0.5% to about 1.5% by weight of the emulsion;

water, from about 65% to about 90% by weight of the emulsion;

clindamycin phosphate, from about 0.5% to about 1.8% by weight of the emulsion;

glycerol, from about 6% to about 18% by weight of the emulsion;

disodium EDTA, from about 0.05% to about 0.2% by weight of the emulsion;

methylparaben, from about 0.1% to about 0.5% by weight of the emulsion;

propylparaben, from about 0.05% to about 0.2% by weight of the emulsion;

sodium hydroxide, from about 0.005% to about 0.05% by weight of the emulsion; and sodium phosphate monobasic, from about 0.1% to about 1.5% by weight of the emulsion;

a propellant; and a purge gas.

10. The method of claim 1, wherein the composition consists essentially of:

an emulsion, wherein the emulsion consists essentially of:

cetostearyl alcohol, in about 2.0% by weight of the emulsion;

emulsifying wax, in about 2.0% by weight of the emulsion;

steareth-10, in about 0.8% by weight of the emulsion;

dimethicone, in about 1.0% by weight of the emulsion;

water, in about 79.7% by weight of the emulsion;

clindamycin phosphate, in about 1.2% by weight of the emulsion;

glycerol, in about 12.5% by weight of the emulsion;

disodium EDTA, in about 0.1% by weight of the emulsion;

methylparaben, in about 0.3% by weight of the emulsion;

propylparaben, in about 0.1% by weight of the emulsion;

sodium hydroxide, in about 0.01% by weight of the emulsion; and sodium phosphate monobasic, in about 0.3% by weight of the emulsion;

a propellant; and a purge gas.

11. The method of claim 1, wherein the composition consists essentially of:

an emulsion, wherein the emulsion consists essentially of:

cetostearyl alcohol, in about 2.0% by weight of the emulsion;

emulsifying wax, in about 2.0% by weight of the emulsion;

steareth-10, in about 0.8% by weight of the emulsion;

dimethicone, in about 1.0% by weight of the emulsion;

water, in about 79.0% by weight of the emulsion;

clindamycin phosphate, in about 1.2% by weight of the emulsion;

glycerol, in about 12.5% by weight of the emulsion;

disodium EDTA, in about 0.1% by weight of the emulsion;

methylparaben, in about 0.3% by weight of the emulsion;

propylparaben, in about 0.1% by weight of the emulsion;

sodium hydroxide, in about 0.03% by weight of the emulsion; and sodium phosphate monobasic, in about 1.0% by weight of the emulsion;

a propellant; and a purge gas.

* * * * *